United States Patent [19]
Blair

[11] Patent Number: 6,088,612
[45] Date of Patent: Jul. 11, 2000

[54] METHOD AND APPARATUS FOR REFLECTIVE GLARE REMOVAL IN DIGITAL PHOTOGRAPHY USEFUL IN CERVICAL CANCER DETECTION

[75] Inventor: Kerry L. Blair, Overland Park, Kans.

[73] Assignee: Medtech Research Corporation, Lenexa, Kans.

[21] Appl. No.: 08/832,802

[22] Filed: Apr. 4, 1997

[51] Int. Cl.[7] .................................................. A61B 5/00
[52] U.S. Cl. ........................ 600/407; 600/425; 600/476; 345/112; 345/501; 348/77; 250/559.05; 250/559.08
[58] Field of Search .................................. 600/407, 425, 600/476, 477; 348/77; 250/200, 559.05, 559.08; 382/128, 130; 345/501, 112

[56] References Cited

U.S. PATENT DOCUMENTS

| | | |
|---|---|---|
| 3,805,596 | 4/1974 | Klahr . |
| 4,300,570 | 11/1981 | Stafl . |
| 4,407,290 | 10/1983 | Wilber . |
| 4,519,684 | 5/1985 | Francis, Jr. et al. . |
| 4,588,294 | 5/1986 | Siegmund . |
| 4,841,555 | 6/1989 | Doi et al. . |
| 4,860,371 | 8/1989 | Matsuyama et al. . |
| 4,888,490 | 12/1989 | Bass et al. . |
| 4,905,670 | 3/1990 | Adair . |
| 5,026,368 | 6/1991 | Adair . |
| 5,036,853 | 8/1991 | Jeffcoat et al. . |
| 5,179,938 | 1/1993 | Lonky . |
| 5,211,938 | 5/1993 | Kennedy et al. . |
| 5,214,456 | 5/1993 | Gersten . |
| 5,215,095 | 6/1993 | Macvicar et al. ...................... 600/476 |
| 5,251,613 | 10/1993 | Adair . |
| 5,309,214 | 5/1994 | Hashimoto . |
| 5,329,938 | 7/1994 | Lonky . |
| 5,413,108 | 5/1995 | Alfano . |
| 5,421,339 | 6/1995 | Ramanujam et al. . |
| 5,450,857 | 9/1995 | Garfield . |
| 5,554,160 | 9/1996 | Caillouette . |
| 5,687,251 | 11/1997 | Erler et al. ............................. 382/133 |

OTHER PUBLICATIONS

Emma Gilmour, M.D., "Measuring Cervical Ectopy: Direct Visual Assessment Versus Computerized Planimetry", *American Journal of Obstetrics & Gynecology*, vol. 176, No. 1, 1997, pp. 108–111.

Paola M. Cristoforoni, M.D., "Computerized Colposcopy Results of a Pilot Study and Analysis of Its Clinical Relevances", *Obstetrics & Gynecology*; vol. 85, No. 6, Jun. 1995, pp. 1011–1016.

M.I. Shafi, "Digital Imaging Colposcopy, Image Analysis and Quantification of the Colposcopic Image", *British Journal of Obstetrics and Gynecology*, vol. 101, Mar. 1994, pp. 234–238.

L. Stewart Massad, "Use of Speculoscopy in the Evaluation of Women with Atypical Papanicolaou Smears", *The Journal of Reproductive Medicine*, vol. 38, No. 3, Mar. 1993, pp. 163–169.

(List continued on next page.)

*Primary Examiner*—Ruth S. Smith
*Attorney, Agent, or Firm*—Lathrop & Gage L.C.

[57] ABSTRACT

An apparatus is disclosed for glare removal in digital imaging of a cervix. The apparatus includes a digital camera operable to create first and second digital images having substantially the same field of view; lights associated with the camera for illuminating the cervix with light pulses emitted from two locations, and a digital processor. The light pulses are synchronized so the cervix is illuminated with a first pulse for the creation of the first image and the cervix is illuminated with a second pulse for the creation of the second image. First glare and first non-glare regions are created by the first pulse in the first image, and second glare and second non-glare regions are created by the second pulse in the second image. The processor creates a glare-free digital composite image by replacing the digital elements of the glare region of the first image with the corresponding digital elements from the non-glare region of the second image.

13 Claims, 13 Drawing Sheets

OTHER PUBLICATIONS

W. Mann, "Papanicolaou Smear Screening Augmented by a Magnified Chemiluminescent Exam", *International Federation of Gynecology and Obstetrics*, vol. 43, 1993, pp. 289–296.

W.P. Soutter, "Computerization of a Colposcopy Clinic", *British Journal of Obstetrics and Gynecology*, vol. 98, Aug. 1991, pp. 824–828.

William E. Crisp, M.D., "The Computerized Digital Imaging Colposcope: Future Directions", *American Journal of Obstetrics and Gynecology*, vol. 162, No. 6, Jun. 1990, pp. 1491–1498.

Vittorio Contini, "Colposcopy and Computer Graphics: A New Method?", *American Journal of Obstetrics and Gynecology*, vol. 160, No. 3, Mar. 1989, pp. 535–538.

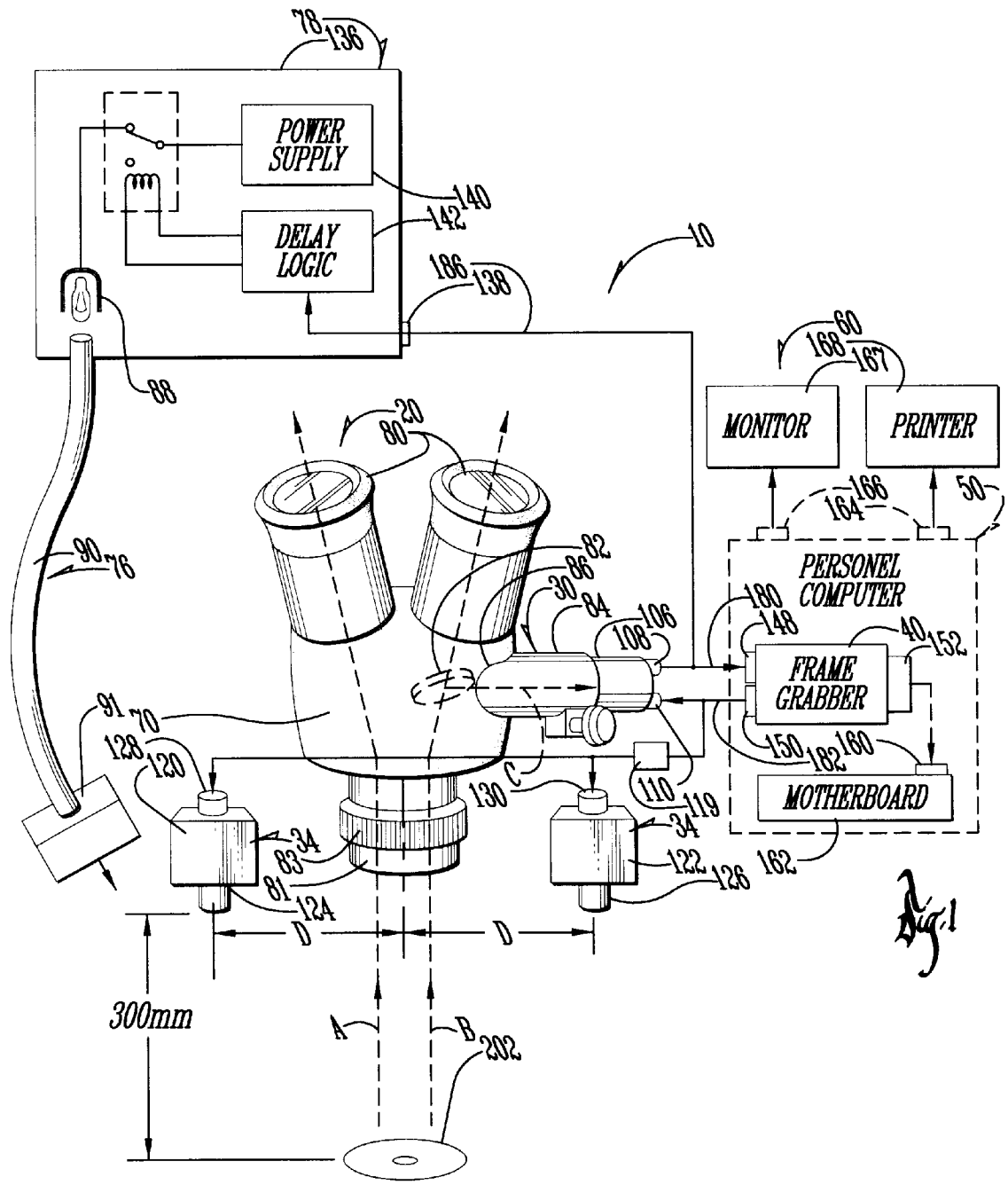

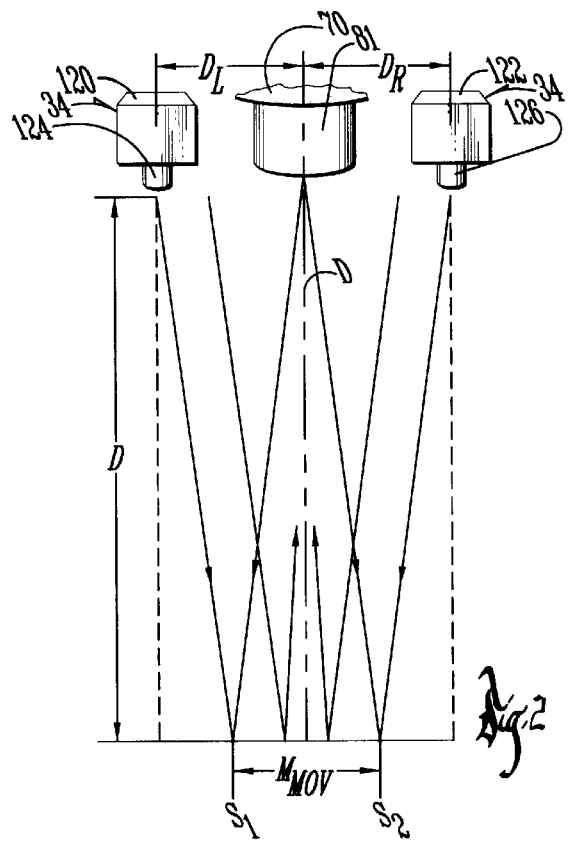
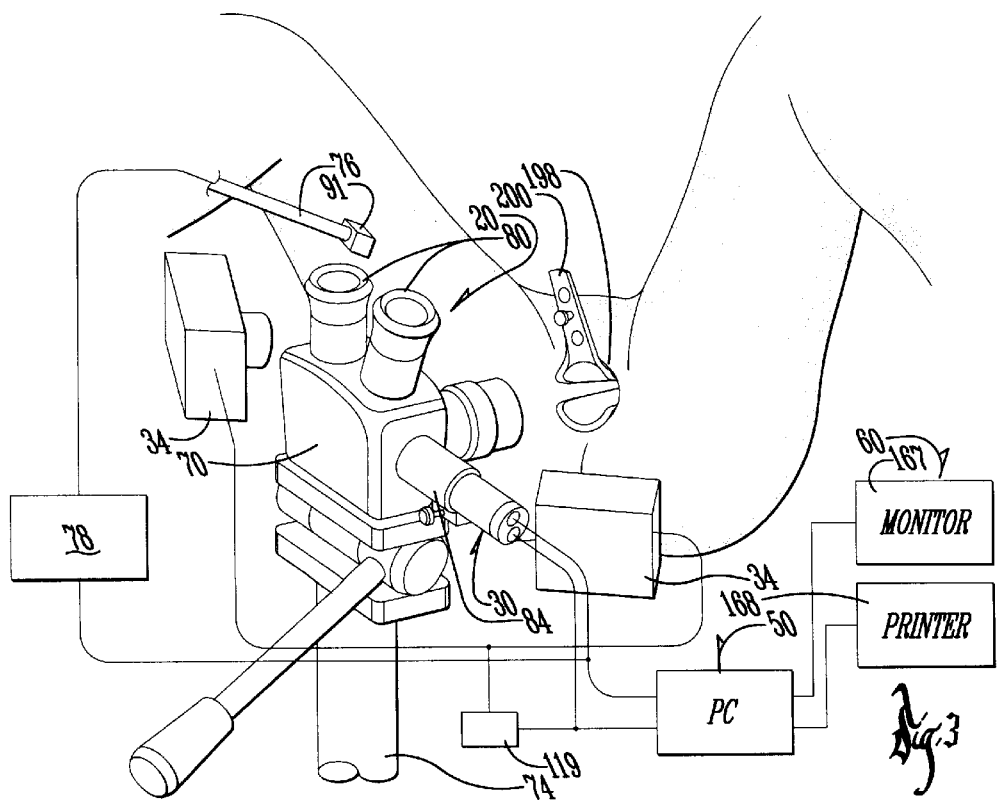

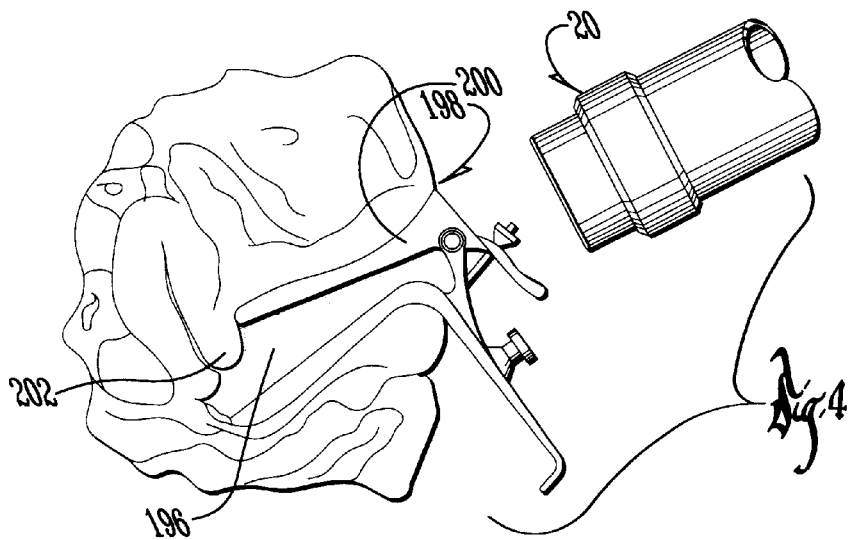
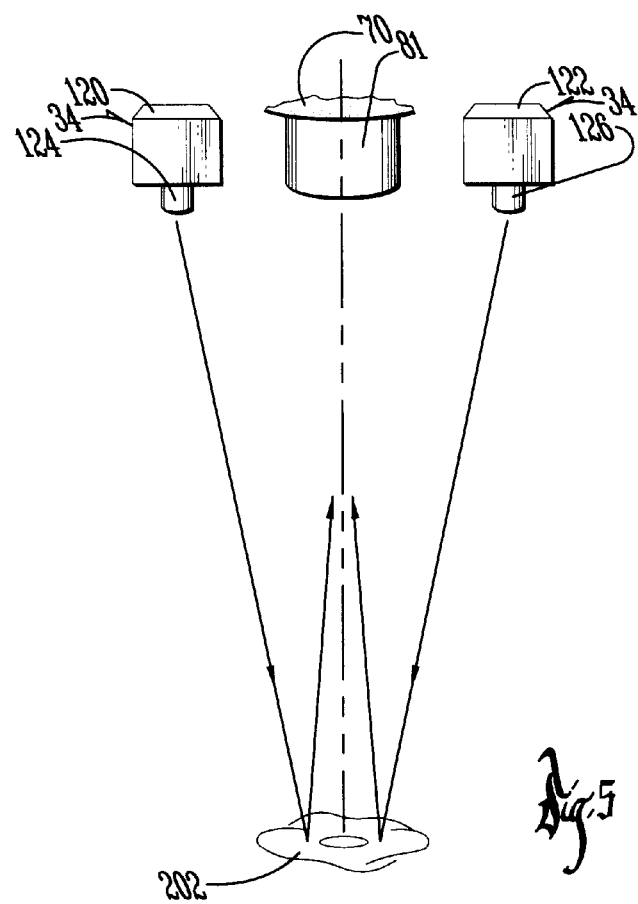

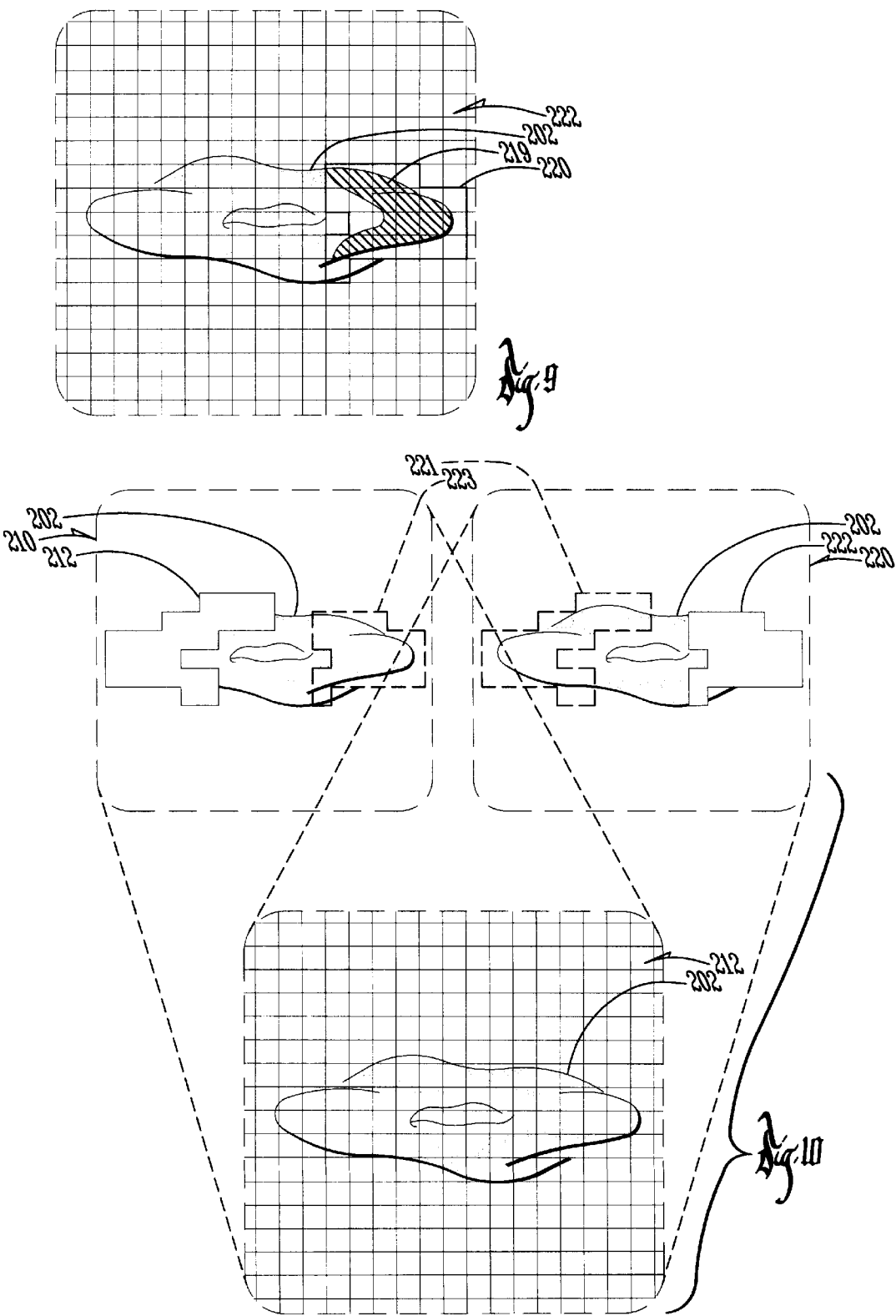

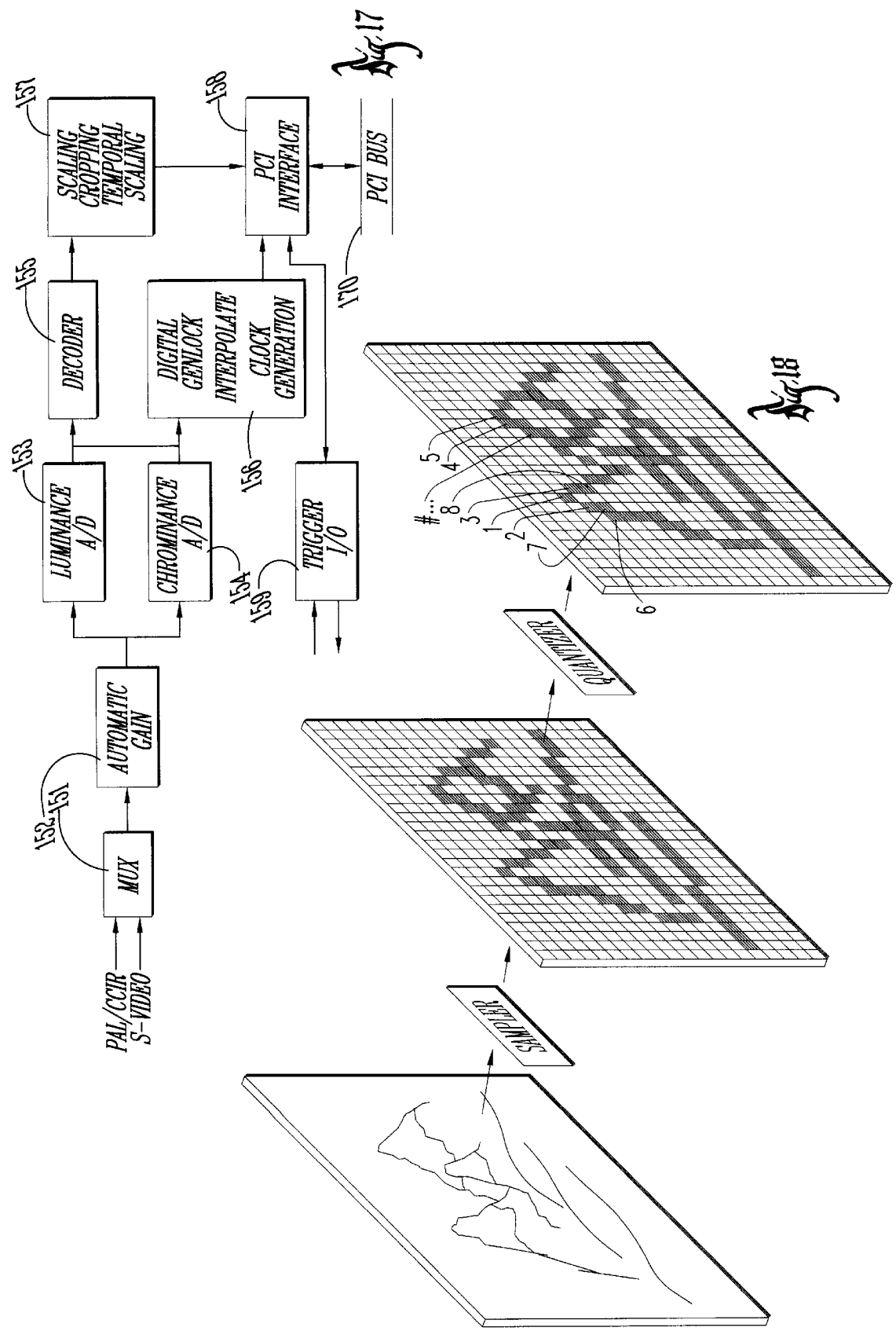

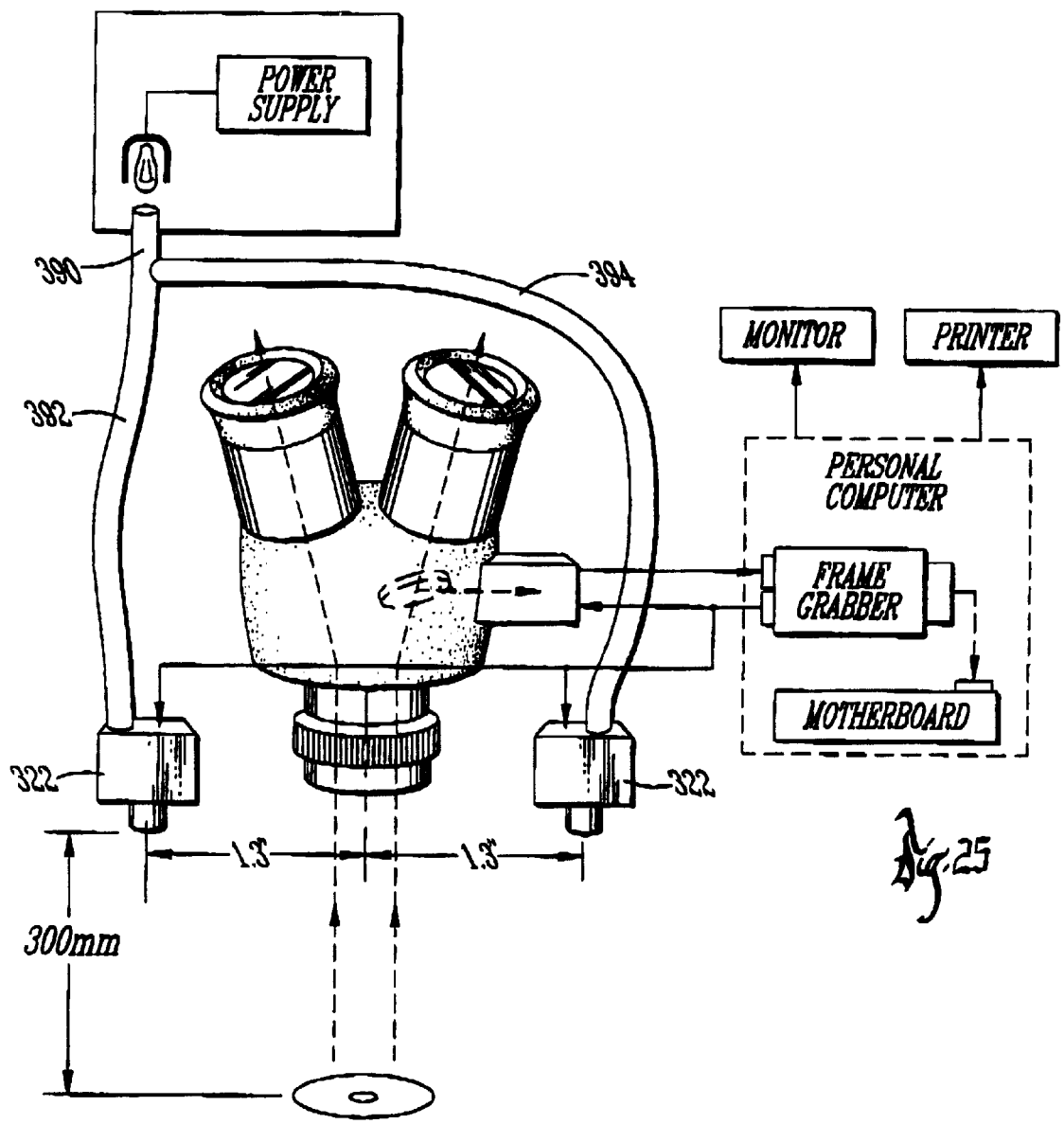

METHOD AND APPARATUS FOR REFLECTIVE GLARE REMOVAL IN DIGITAL PHOTOGRAPHY USEFUL IN CERVICAL CANCER DETECTION

1. BACKGROUND OF THE INVENTION

1.1. Field of the Invention

Present invention relates generally to the detection of cervical cancer. More particularly, the present invention relates to an apparatus and method for the visual examination of cervical epithelium by means of a colposcopy assembly capable of producing a digital image of the cervix which is essentially free of reflective glare that otherwise masks or veils cancerous and pre-cancerous tissue.

1.2. Problems in the Art

1.2.1 General Setting of the Invention

Over the last fifty years, Papanicolaou Smear ("Pap Smear") has become the cornerstone of efforts to reduce cervical cancer mortality. Pap Smear is effective because it identifies the latest stages of cervical cancer. Current estimates are that 60–70 million Pap Smears are done in the U.S. each year. Pap Smear has, thus, become a norm in the detection of cervical cancer. In spite of its broad acceptance in the medical community, studies indicate that Pap Smear screenings will fail to detect from 50%–80% of low grade cancerous lesions, and even 15%–30% of high grade cancerous lesions.

1.2.2 Conventional Methods and Systems

When conducting Pap Smear screenings, the gynecologist collects exfoliated cells from the surface of the cervix and places them on slides that are sent to cytologists for further examination. Cytologists then review the cells placed on the slides and look for abnormal cells. If abnormal cells are found, the Pap Smear is considered to be positive. If no abnormal cells are found, the Pap Smear is considered to be negative. It is also possible that Pap Smear slides cannot be properly evaluated by the cytologist because of technical problems associated with the Pap Smear collection process such inadequate cell count, improper slide fixation, etc.

In the early stages of cervical disease, abnormal cell exfoliation is slow and most abnormal cells are located below the surface or are trapped by a keratin barrier covering the cervical surface. In these circumstances, the Pap Smear screening process is a relatively insensitive indicator of cervical health due to inaccessibility of abnormal cells that are otherwise indicators of cancerous or pre-cancerous tissue. HPV virus is the most common cause of keratin barriers to exfoliation. Further, it is commonly known that a significant portion of the U.S. population harbors the HPV virus which therefore, complicates the challenge of cervical cancer detection when using the Pap Smear as the principal screening procedure.

Because of a variety of problems associated with Pap Smear screening, it is well known that the Pap Smear procedure has both a high false negative, and a high false positive rate. Nevertheless, in spite of its cancer detection shortcomings, Pap Smear screening has become generally recognized as a practical and economical procedure for the early detection of cervical cancer. While the Pap Smear process is designed for initial screening, colposcopy, and related procedures, are generally used to confirm Pap Smear abnormalities and to grade cancerous and potential cancerous lesions.

Since its introduction in 1925, colposcopy has acquired wide recognition as a follow-up clinical procedure for patients identified by Pap Smear screening as having possible cervical abnormalities. It is generally recognized that colposcopy is highly effective in evaluating patients with abnormal Pap Smears and has therefore become the standard of medical care in the Western world for this circumstance. It is estimated that approximately 4 million colposcopy examinations are currently performed in the U.S. each year. Its routine use, however, is time consuming and costly. Further, proper colposcopy examinations are limited by the expertise of the examiner.

The recent emergence of computer-aided colposcopy creates a potential for the enhancement of colposcopic assessments. Computer-aided colposcopy provides for expanded utility in digital colposcopic photography and videography, and in the management of information generated by the colposcopic examination, including computer-aided processing and enhancement of colposcopic-generated images. Computer-aided colposcopy also sets up a platform that will facilitate the emergence and development of "telemedicine" by permitting the communication of diagnostic digital image information across tele-communication networks.

1.2.3 Shortcomings—Needs

Colposcopy, however, is faced with its own set of challenges. It is a subjective assessment and the quality depends greatly on the expertise of the practitioner. It is time consuming with significant legal risks associated with false negative evaluations, and is therefore expensive. Computer-aided colposcopy, while capable of generating, storing and manipulating image data for the production of high-quality images, is suffering certain technical difficulties. One of the greatest difficulties encountered is glare resulting from the reflection of colposcopic illumination from wet cervical tissue and its associated derogatory effect on visualized and captured image quality. Technical difficulties resulting from reflective glare have been reported in the literature as responsible for significant percentages of computer-aided colposcopic captured images rendered unreadable. In situations where traditional film photography-aided colposcopy have been evaluated, it has been similarly reported in the literature that a significant portion of photographic images are rendered unusable because of glare artifacts produced as a result of the reflections from the illumination used in the photographic image creation process.

Another difficulty is the formation of shadows from unevenly disbursed lighting used to illuminate the vaginal cavity for examination. Shadows either veil or distort the appearance of the area under examination.

Another difficulty with traditional photography-aided colposcopy is the long delay from the time a photograph is taken until it is developed so that photographic image may be seen. This delay is overcome with Polaroid film photography, but at the cost of an inability to produce high quality copies from the original. With such a delay, the patient may not be conveniently available to take another photograph in the event that the previous one was defective.

A two-fold need, therefore, exists in the area of cervical cancer screening and detection. A simple, low-cost colposcopic technique is needed for use in conjunction with the Pap Smear procedure that would improve the overall statistical accuracy of the screening effort. In addition, traditional colposcopy should be made easier to perform by reducing the subjectivity of the examination and should further be capable of producing archivable images that are devoid of technical flaws and inadequacies.

1.3. Objects, Features and Advantages of the Invention

In accordance with the present invention, a method and apparatus are disclosed for the removal of reflective glare from digital colposcopic photography and videography. The present invention enables real-time imaging and archiving of images of the entire cervix for the purpose of detecting cancerous and pre-cancerous tissue.

Thus, an object of the present invention is to provide a computer-aided colposcopy device, a so-called "digital colposcope," having non-invasive, digital camera capability that provides for glare removal and general image enhancement, documentation, and an image archival means.

Another object of the invention is to provide a unique light source for illumination of the cervical tissue during digital image generation.

Another object of the invention is to provide a wireless computer interface capability between the digital colposcope and a computerized digital image archival system.

Another object of the invention is to provide such a digital colposcope with improved screening and diagnostic capability, and which is useful to grade lesion severity that may be otherwise obstructed by glare.

Another object of the invention is to employ digital photographic techniques with the computer processing and display technology in order to provide relatively instantaneous presentation of the digital photographic image on a color computer display. Such display and computer being an integral part of the digital colposcope. This rapid feedback of image quality would allow a doctor to re-take any digital photographic images that were deemed unsatisfactory.

Another object of the invention is to physically mount the computer display in on the colposcope in a fashion that would allow the patient to view the digital photographic colposcopic image so that the doctor might better educate the patient as to the medical conditions of the colposcopic view.

2. SUMMARY OF THE INVENTION

These and other objects of the invention are attained by the invention disclosed below. According to the invention, an apparatus and method for glare removal in digital colposcopy and videography is provided that comprises a digital imaging camera that is operably coupled to the optical path of the digital colposcope by means of a beam splitter so that a first and second digital image of the cervix can be captured in rapid sequence.

A strobe light assembly is operably coupled to the digital camera and is capable of emitting pulses of light from two separate locations and is synchronized so that a first pulse of light illuminates the cervix when the first image is created and a second pulse of light illuminates the cervix when the second image is created. The first and second images each comprise a matrix of digital elements and a cervical image region is formed in substantially identical digital elements of each image matrix. Glare and non-glare regions are also formed in each image matrix. The distance separating the strobe lights is preferably sufficient so that glare regions formed in individual digital image matrixes do not overlap. A digital processing means is provided and is operable to create a glare-free digital composite image by replacing the matrix elements associated with the glare region of one image with the corresponding matrix element from the non-glare region of the other image.

3. BRIEF DESCRIPTION OF THE DRAWINGS

FIG. 1 is a diagram of an exemplary system designed in accordance with the present invention;

FIG. 2 is a diagram illustrating the optical path of the colposcopic and the strobe light assembly;

FIG. 3 is a perspective view of the apparatus of the present invention positioned for taking a photograph of the cervix;

FIG. 4 is a schematic view, partially in cross-section, of the vaginal area showing the optical path of the inventive apparatus;

FIG. 5 is a schematic diagram of the apparatus photographing a cervix;

FIGS. 6–11 are representations of cervix images produced by the apparatus;

FIG. 17 is a block diagram of a PIXCI imaging board;

FIG. 18 is a representation of a digitalization process;

FIG. 25 is a schematic diagram of an alternative embodiment of the apparatus.

4. DETAILED DESCRIPTION OF THE INVENTION

Figure 6:
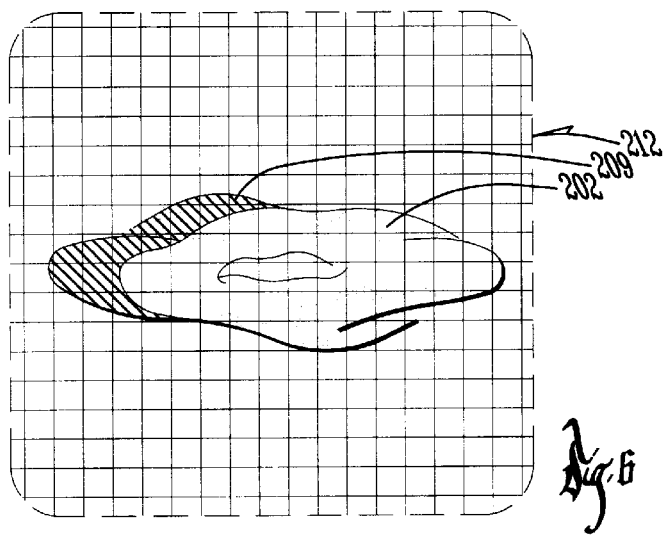
Figure 7:
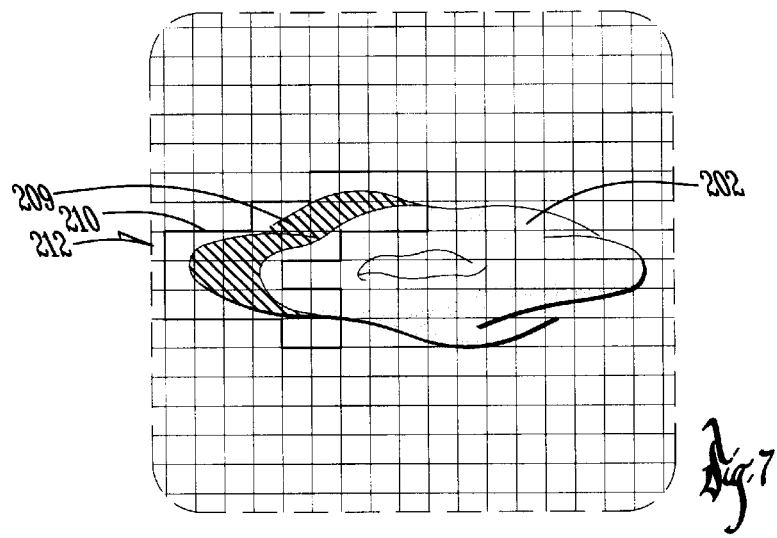
Figure 8:
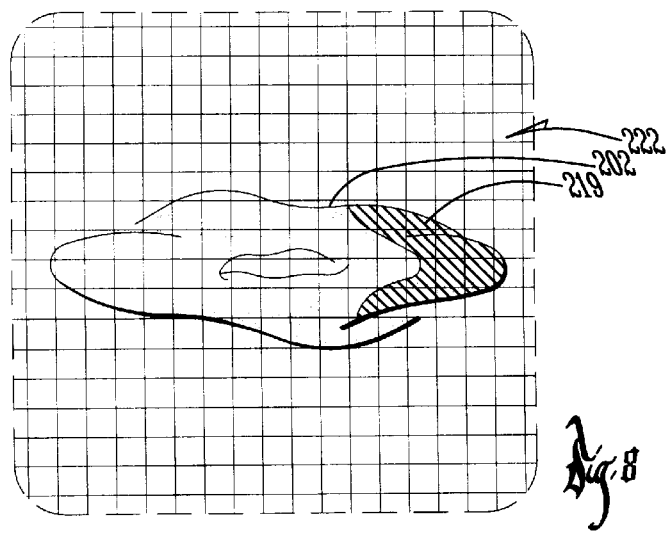

In the following description of preferred embodiments of the invention, particular reference will be made to methods and apparatus for optically imaging cervical tissue that is being analyzed for cancerous abnormalities. It will be appreciated by those skilled in the art that the present invention is not limited to such treatment, but can be equally applied to imaging of any mammalian tissue for the identification of cancerous and pre-cancerous abnormalities.

4.1. Overview—The Inventive Colposcopy System

Referring first to FIG. 1, the apparatus of the invention is generally designated by the numeral 10. Apparatus 10 includes a colposcope 20, a digital imaging means in the form of a digital camera 30, a strobe light assembly 34, a frame capturing means in the form of a frame grabber 40, a digital processing means in the form of a computer 50, and computer peripherals 60.

Colposcope 20 includes a colposcope head 70, extension arm assembly and a stand assembly (not shown), a light source 76, and control panel 78. The colposcope head 70 includes a pair of oculars 80, lens 81, a beam splitter 82, focusing assembly 83, video output 84, and camera mounting structure 86. Main lamp assembly 76 includes a conventional colposcope light 88, an optics fiber 90 operably attached at one end to control panel 78 and at the other end to lighting lens assembly 91. Lighting lens assembly 91 includes a mirror and lens (not shown) operable to illuminate an object for viewing through the colposcope head 70. Lighting lens assembly 91 is mounted to the colposcope head 70 as shown in FIG. 3.

Extension arm assembly 72 includes articulated structure and is pivotally and swingably mounted at one end to colposcope head 70 and at its opposite end to a conventional stand assembly. The lower end of the stand assembly is configured with a rollers that permits easy and convenient movement of colposcope 20.

In a preferred embodiment, colposcope 20 provides a stereo vision, microscopic perspective view of cervical topology through the combination of a pair of optical paths A and B, as shown in FIG. 1. A third optical path is provided by beam splitter 82 placed in one optical path, for example optical path B, to split and direct the image along a third optical path C into the video output 84.

Control panel 78 includes housing 136, input port 138, power supply 140, delay logic system 142, and colposcope light 88.

Frame grabber 40 is designed as a personal computer peripheral card of conventional design and includes video input 148, control output 150, and data input/output 152. In the preferred embodiment, the data input/output bus is accomplished via an industry standard PCI bus as interfaced to a Pentium® personal computer. Referring to FIG. 17, a block diagram of a PIXCI™ frame grabber computer peripheral card is presented. The frame grabber imaging board includes a multiplexer 151, an automatic gain 152, a luminous A/D converter 153, a chrominance A/D converter 154, decoder 155, digital genlock/interperlate clock generation feature 156, a scale cropping temporal scaling feature 157, a PCI interface 158, and a trigger I/O 159. The frame grabber 40 in a preferred embodiment is an Epix Corporation, and is capable of grabbing any one frame of a continuous sequence of frames from video output generating frames at 30 frames per second. Frame grabber 40 also preferably includes a synchronize trigger feature, and memory buffers.

Computer 50 is of conventional personal computer design and has, in the preferred embodiment, the following processing features: a 166 Mhz Pentium micro processor, 32 Mbytes of RAM memory, hard drive disk storage capability, and an RGB color output capability. For the purposes of disclosing the invention, however, Computer 50 is disclosed in terms of a input data 160, mother board 162 (containing the Pentium or other microprocessor), printer output 164, monitor output 166, and bus 170 that is preferably a PCI bus, but may also be an ISA bus. It is understood, however, that computer 50 comprises all other features and functionalities that are well known to be associated with personal computers. Peripherals 60 include monitor 167 and printer 168.

In the preferred embodiment, the colposcope 20 can be obtained from Cooper Surgical, 15 Forest Parkway, Shelton, Conn. 06484, and can be either model OZM-230 or OZM-310, which are models with magnification ranging from 2.8× up to 24×, working distance fields of view ranging between 98.5 mm and 5.6 mm and depths of field of either 230 mm or 310 mm and that include a variable zoom optics system. The main lamp for the Cooper Surgical colposcope used in the example is a 150 w, halogen fiber optics source with variable intensity. The optics system in the colposcopic head 70 includes a red-free green filter. The colposcope head may be adjusted to a height of between 37" to 57". As shown in FIG. 3, when used to conduct a pelvic examination the colposcope head 70 is oriented so that the lens is directed to the vaginal area making the vaginal cavity visible through oculars 80. The operation of a conventional colposcope 20, as used in an examination as shown in FIG. 3, is oriented such that an image of the entire cervix can be obtained.

Digital camera 30 is of conventional design, and in the preferred embodiment, is a Coopers Surgical brand HS4000 brand having a one-half inch CCD image sensor, CCD chip size of 4.6 mm. (H)×4.8 mm (V), picture elements: 768 (H) by 494 (V) or 752 (H) by 582 (V), a 2:1 interlaced scanning system, a 1.5 Lux/F 1.2 (3200k) minimum illumination, 500 TV lines resolution, better than 45 db (AGC OFF) signal to noise ratio, a power supply DC 12 V/250 mA, a C/CS lens mount, dimensions: 50.5 (W)×50.5 (H)×145 (D) mn, wt=450 g. and has the following connectors: video-VMC or via 9 pin D-SUB plug; power-DC-JAK or via 9 pin D SUB plug; auto iris: 4 pin mini jack; and ext. sync-9 pin D-SUB plug.

Figure 15:
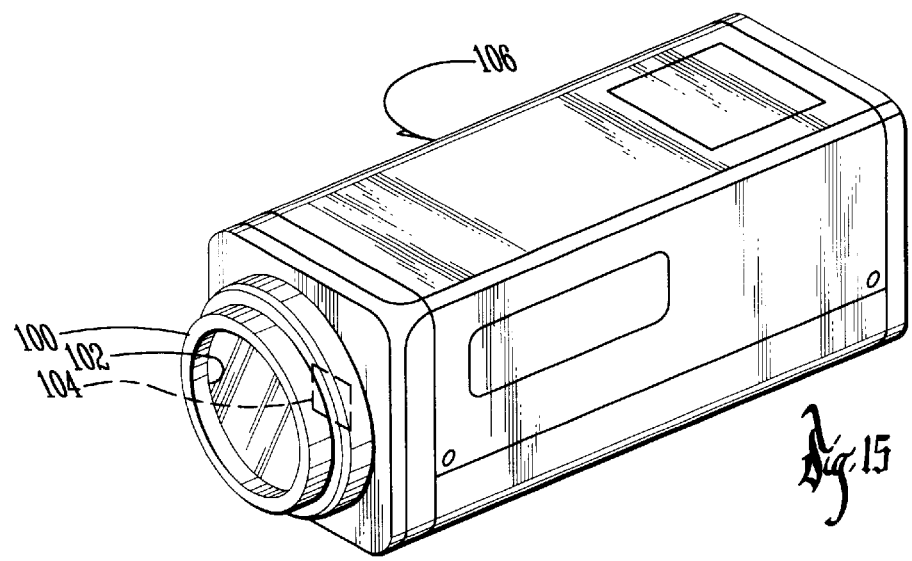
FIG. 15 is a perspective of a digital camera employed in the present invention.
Figure 16:
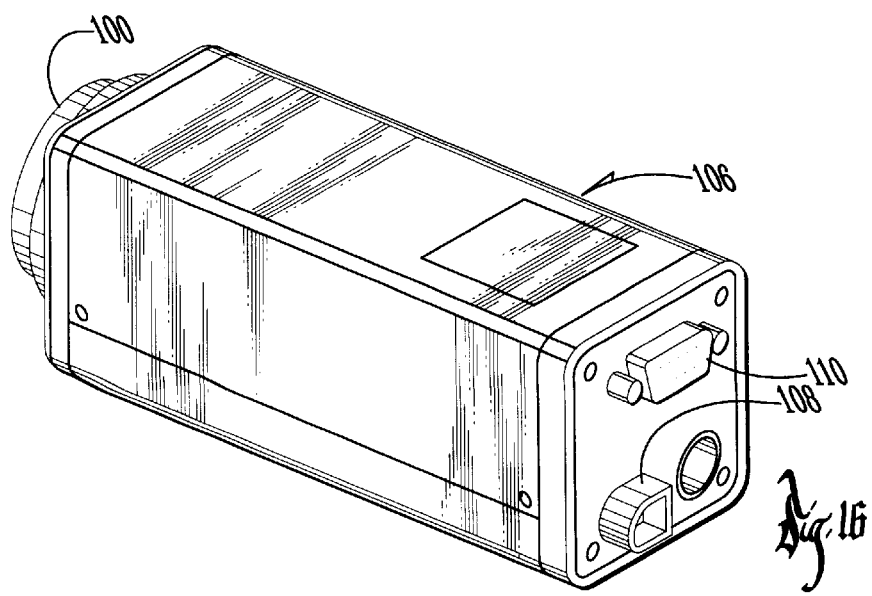
FIG. 16 is a perspective of a digital camera employed in the present invention.

Camera 30, as shown in FIGS. 15–16, includes lens mount 100, image sensor opening 102, CCD chip 104, camera housing 106, video output port 84, and camera input port 110. In the preferred embodiment, camera 30 employs a single CCD chip for image creation when processing. The invention, however, may be practiced with a camera making use of multiple CCD chips.

Referring to FIG. 1, strobe light assembly 34 includes a first strobe light 120 and second strobe light 122, each having light emission ports 124, 126, respectively, and input ports 128, 130, respectively.

Digital camera 30 is adjustably secured to colposcopic head 70 by joining camera lens mount 100 of camera 30 to mount structure 86 of head 70. Camera 30 is mounted to head 70 in such an orientation so as to place CCD chip 104 into optical path c reflected from beam splitter 82 and is brought into proper focus by focus assembly 83. Camera video output 84 is supplied via line 180 to frame grabber input 148. Frame grabber control output 150 is connected to camera input 110 via line 182. Line 184 joins line 182 and provides appropriate signals and power to strobes 124, 126 via strobe inputs 128, 130. Line 186 joins line 182 and provides a signal to relay logic control 142 via control panel input port 138.

4.2. Creation of Digital Images of Vaginal Cavities—The Technique

A general description of conventional techniques for the creation of digital images as employed by apparatus 10 will now be provided.

4.2.1 Creation of Digital Images Generally.

Processes and equipment associated with the generation of digital images are well known in the art and are described in references such as Baxes, G. A., "*Digital Image Processing,*" John Wiley & Sons (1994) (ISBN 0-471-00949-0) Awcock, G. W. and Thomas, R., "*Applied Image Processing,*" McGraw-Hill, Inc. (1995) (ISBN 0-07 001470-1); Russ, J. C., "*The Image Processing Handbook,*" CRC Press (2nd Ed. 1995) (ISBN 0-8493-2516-1).

Non-digitized images, such as conventional photographs, are comprised of continuously varying shades and colors. The shades vary from light to dark and the colors vary from red, green, to blues.

A digital image is composed of discrete levels of gray tone ("brightness"), as opposed to the continuously varying tones associated with non-digitized conventional photographs. A digital image is created from a continuous tone image by dividing it up into individual points of brightness. (See FIG. 18) Each point of brightness is converted into a digital data value. The process of digitizing an image is called "sampling," and the process of converting each discrete sampled item into a digital value is call "quantization." The sampling process samples the intensity of the continuous-tone image at specific locations. The quantization process determines the digital brightness values of each sample ranging from black, to grays, to white. The quantized spacial sample is referred to as a picture element, or "pixel." The processes of sampling and quantization are collectively referred to as image digitization.

Figure 19:
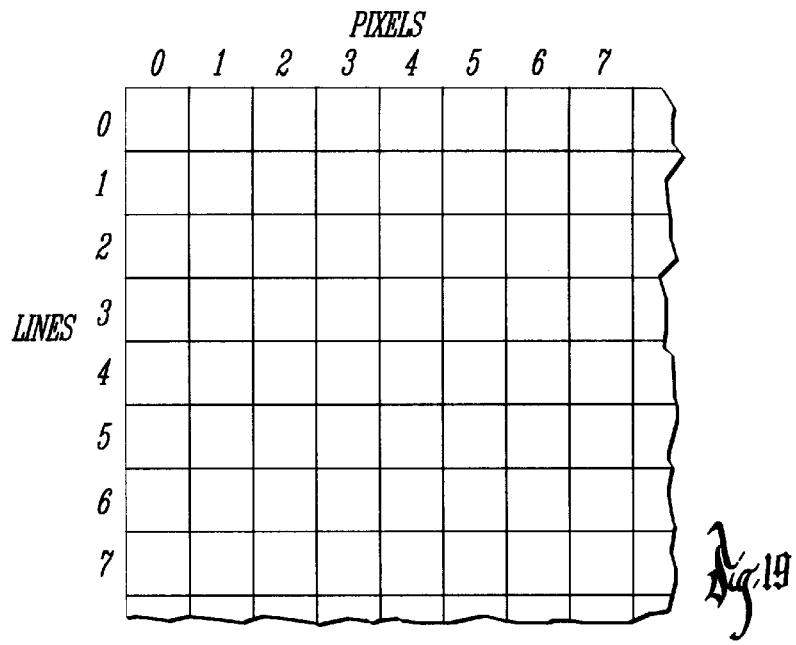
FIG. 19 is a representation of a pixel array.

Referring to FIG. 18, in image digitization, an image is generally sampled into a rectangular array of pixels 186. Each pixel has its own (x, y) coordinate that corresponds to its location within the rectangular array that comprises the image. Once sampled and quantitized, each pixel will have generated an output quantity that is proportional to the input lighting intensity. Image resolution is thus a function of the number of pixels that make up the rectangular array and the capability of the digital image to resolve the elements, as closely as possible, to the original scene. The pixel arrays are traditionally orthogonal (Cartesian geometry) such as that shown in FIGS. 18 and 19. Arrays, however, may also have an hexagonal configuration. See, e.g., Awcock, et al., *"Applied Image Processing,"*.

With charge couple device technologies ("CCD"), it is possible to place more than 300,000 pixels in an area of less than one square centimeter. More specifically, there are 307,200 pixels in a conventional 640×480 array. Each pixel of a CCD functions as a detector of light intensity, and more specifically as a photo counter, as electrons are raised to the conduction band in an isolated well.

Figure 20:
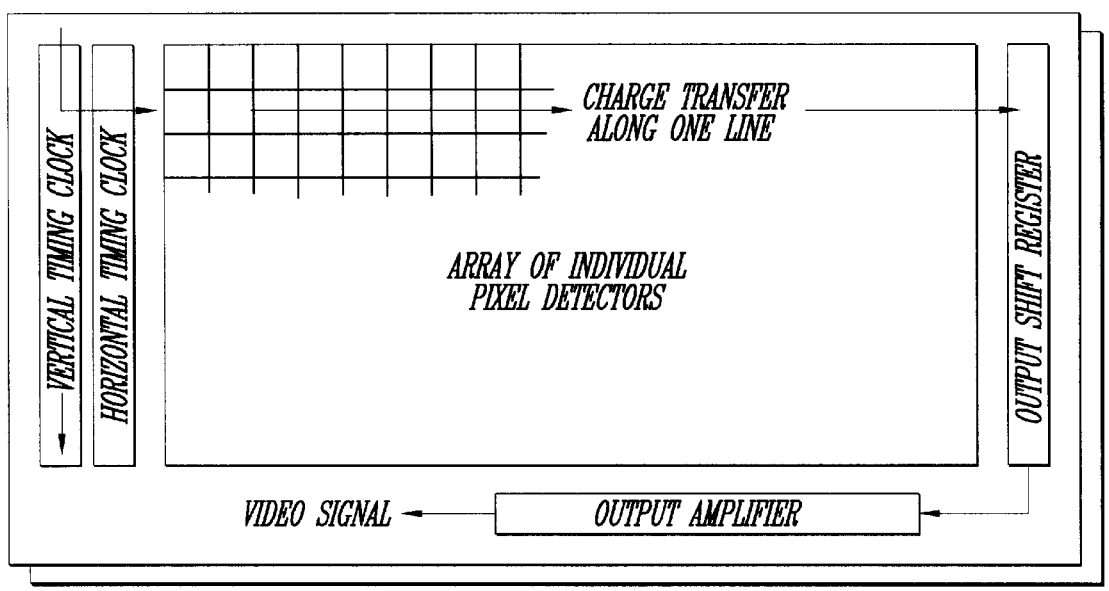
FIG. 20 is a representation of pixel charge transfer.

Referring to FIG. 20, a signal is read out from each line of detector pixels to produce an analog voltage. FIG. 20 shows a schematic diagram of a typical CCD camera chip. A vertical timing clock selects each line of pixel detectors in turn. Then a horizontal clock shifts the contents from each detector to its neighbor, causing the line to read out sequentially into a shift register and amplifier that produces an analog voltage as a function of time. Specific CCD array architectures include (a) parallel/serial; (b) interlined transfer; and (c) frame transfer.

Figure 23:
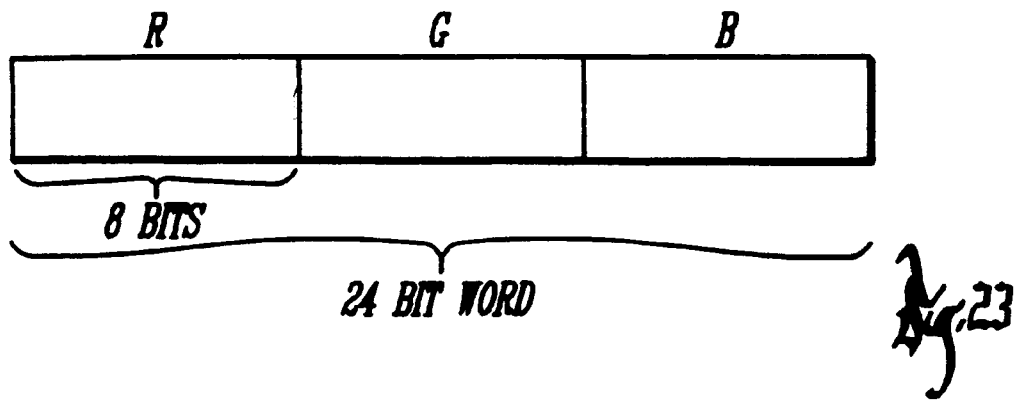
FIG. 23 is a schematic of a 24 bit word for use in color digital imaging.

The process previously described for the generation of digital images also applies to color images. In a single CCD chip comprised of a rectangular array of pixels capable of generating a color image, pixels in each line are constructed with filters such that every third pixel in each line detects red, blue, and green light. A single color CCD chip will be composed of detector pixels in repeating sequential groups of red, green, and blue detectors. Thus, if each detector has a gray-scale of $2^8$, it will create an analog output between 0 and 255 that is proportional to the red, green, or blue light intensity striking the particular detector. Further, as schematically shown in FIG. 23, each pixel consisting of a red, green, and blue detector are represented by a 24-bit word.

In digital imaging, a wide range of colors can be created by mixing red, blue, and green in various combinations, and are well developed in the art. See, e.g., Baxs, *"Digital Imaging Processing,"* at 53–56.

It will thus be appreciated that the processes described herein for monochrome digital imaging can be employed in color digital imaging by first converting the 24-bit color words in the pixel array rectangle into individual color intensity values. The conversion process applied in reverse is then used to recreate a color digital image using color intensity values.

4.2.2 The Operation of the Inventive Digital Colposcope 4.2.2.1 Creation of Digital Images Having Substantially Identical Fields of View But Having Different Glare Regions.

A central aspect of the invention will now be described that is associated with the use of inventive digital colposcope to create at least two images having the same field of view but which display different regions of reflective glare.

As used herein, glare is defined to mean that condition of detector/pixel saturation caused by a sufficiently high intensity of light shining on the detector. The light intensity required to illuminate the irregular surfaces of a vaginal cavity often creates regions of glare in digital images produced of the vaginal cavity. In the practice of the invention, therefore, it is necessary to create at least two digital images with substantially identical fields of view but with glare, should it occur, in different regions of each image.

The inventive technique and equipment used for this purpose is schematically illustrated in FIG. 2. A colposcope lens 81 is positioned between first and second strobes 120, 122, separated by a distance $D_L$ and $D_R$, respectively. If strobes 120, 122 are oriented such that their light paths reflect from the surface and back into the optical path d of lens 81, as shown in FIG. 2, regions of glare will be created at locations $S_1$ and $S_2$ on the surface. (The exact shape of the glare regions created will depend upon the surface contour, surface conditions-wet or dry, and light intensity.) The distance $M_{mov}$ that separates the center of the glare regions is a geometric function of distances $D_L$ and $D_R$. Thus, to insure that the glare region created by strobe 120 does not overlap with glare region created by strobe 122, at a given light intensity, the position of the strobes need merely be separated by a sufficient distance.

The same concept applies to the illumination of the vaginal cavity. That is, when the colposcopic head 70 is oriented for viewing of the vaginal cavity so that the cervix is within its field of view, strobes 120, 122 should be separated by sufficient distance so that any glare regions created by each strobe light does not overlap in the digital image, but not so far separated so as to have an obscured view of the cervix.

4.2.2.2 Selection of Colposcopy Optics

It will be appreciated by those skilled in the art that it will be beneficial to select colposcopy optics and strobe lighting so that regions of illumination in the digital images represent an appreciable portion of the field of view of the digital colposcope-but without creating overlapping glare regions-thus maximizing the extent to which the vaginal cavity may be illuminated with a minimum of shadows.

4.2.2.3 Operation of Inventive Colposcope to Produce Digital Images of a Cervix

Referring to FIGS. 1–4, colposcope 20 is positioned so that head 70 is oriented in the vaginal region to permit viewing into the vaginal cavity 196 through the vagina 198 into which a speculum 200 is inserted in the vagina 198 and is adjusted so that the cervix 202 will be in view. By viewing the cervix 202 through oculars 80, colposcope head 70 is aligned so that cervix 202 is centered on optical paths A and B (FIG. 1) and is adjusted so that the cervix 202 is viewed in its entirety.

To assist with the proper alignment of colposcopic head 70, main lamp assembly 76 is switched on so that light 88 travels along optics fiber 90 and is redirected through lighting lens assembly 91. Assembly 91 is mounted to head 70 so that it illuminates objects in optical path C. Head 70 is typically located so that the cervix is about 300 mm from lens 81, in order to provide a convenient work, distance for the placement of colposcopic hand utensils such as biopsy punches. This distance may, of course, vary when different optical systems are selected for desired viewing characteristics and functionalities.

With the cervix 202 properly positioned within optical paths A and B of head 70, as shown in FIG. 1, beam splitter 82 can be employed to direct a split beam along optical path C and through camera opening 102 so that the image of cervix 202 will be directed upon CCD chip 104. Appropriate optics are selected and adjusted so that the image of the cervix is focused on CCD chip 104 to achieve the desired results. For example, it is typically preferable that the cervix 202 image comprise substantially the entire rectangular pixel array that comprises CCD chip 104.

Camera 30 is operable to generate a video image output of cervix 202 that comprises the generation an output at the rate of 30 image frames per second. It will be appreciated, however, that the invention can be practiced with video outputs generated at different rates.

The video output exits camera output port 106 and is directed to frame grabber video input port 148 via line 180. Frame grabber 40 is operable to asynchronously select any of the video images created by camera 30 and generate a image signal which exits the frame grabber 40 through data output port 152 and is sent to mother board 162 via bus 170. Mother board 162 of computer 50 is then operable to archive an image for any desirable purpose, including enhancement, documentation, archival, or transmission to other destinations. Computer 50 is further operable to reproduce a digital image of cervix 202 on monitor 167 or in hard copy by means of reproduction of image by printer 168.

4.2.2.4 Operation of Strobe Light Assembly

Figure 24:
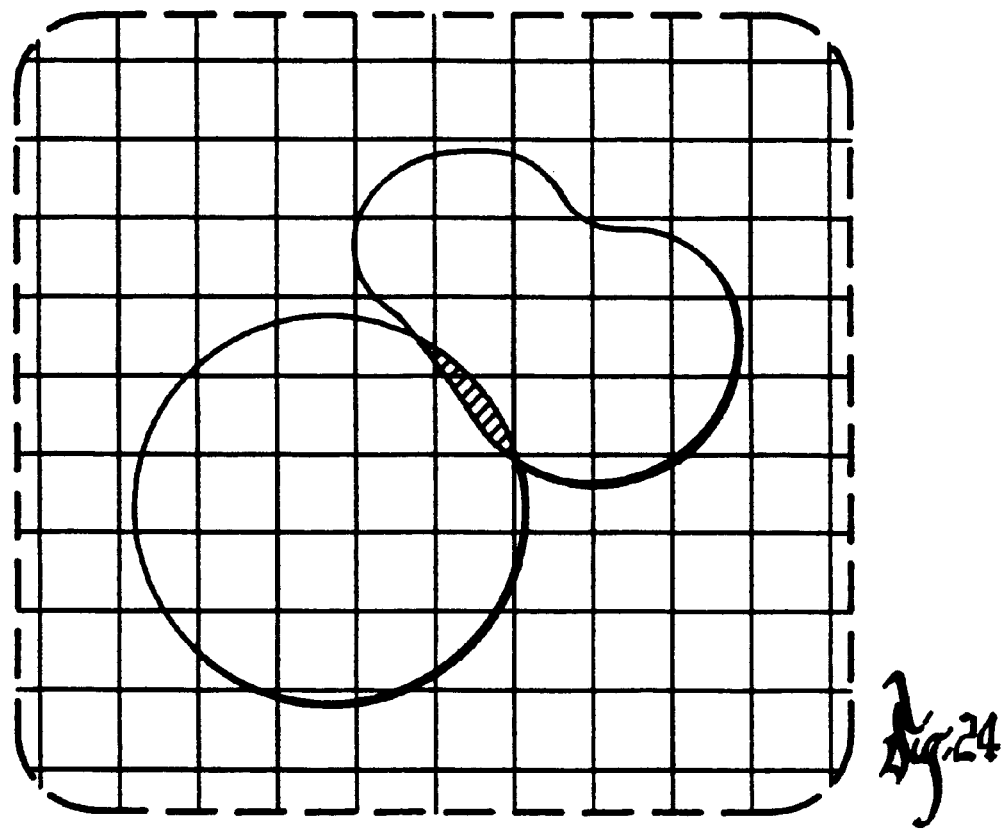
FIG. 24 is a representation of cervix images with partially overlapping glare regions produced by the apparatus.

Referring now to FIGS. 2, 6–11, strobes 120, 122 are separated from lens 81 by distance $D_L$, $D_R$, respectively, so that a glare region 210 (FIG. 7) appearing in a first digital image 212 created with illumination by strobe 120 has a location in the image different from a glare region 220 (FIG. 9) appearing in a second digital image 222 created with illumination by strobe 122. Although it is preferable in the practice of the invention to create images with non-overlapping glare regions, it will be understood by those skilled in the art that the invention has glare-removal utility even when glare regions overlap as shown in FIG. 24.

As described above, frame grabber 40 is operably connected to camera 30 and strobe controller 119 so that frame grabber 40 signals strobe controller 119 to cause strobes 120, 122 to emit pulses of light to illuminate cervix 202 for the creation of first and second digital images 212, 222 (FIGS. 6–9). To achieve this purpose, trigger I/O 159 of frame grabber 40 provides input signals to strobe input ports 128, 130 of strobe lights 120, 122, respectively. Input signals are passed from ports 128, 130 to trigger gate inputs TRIG1, 2, shown in FIG. 22.

Figure 22:
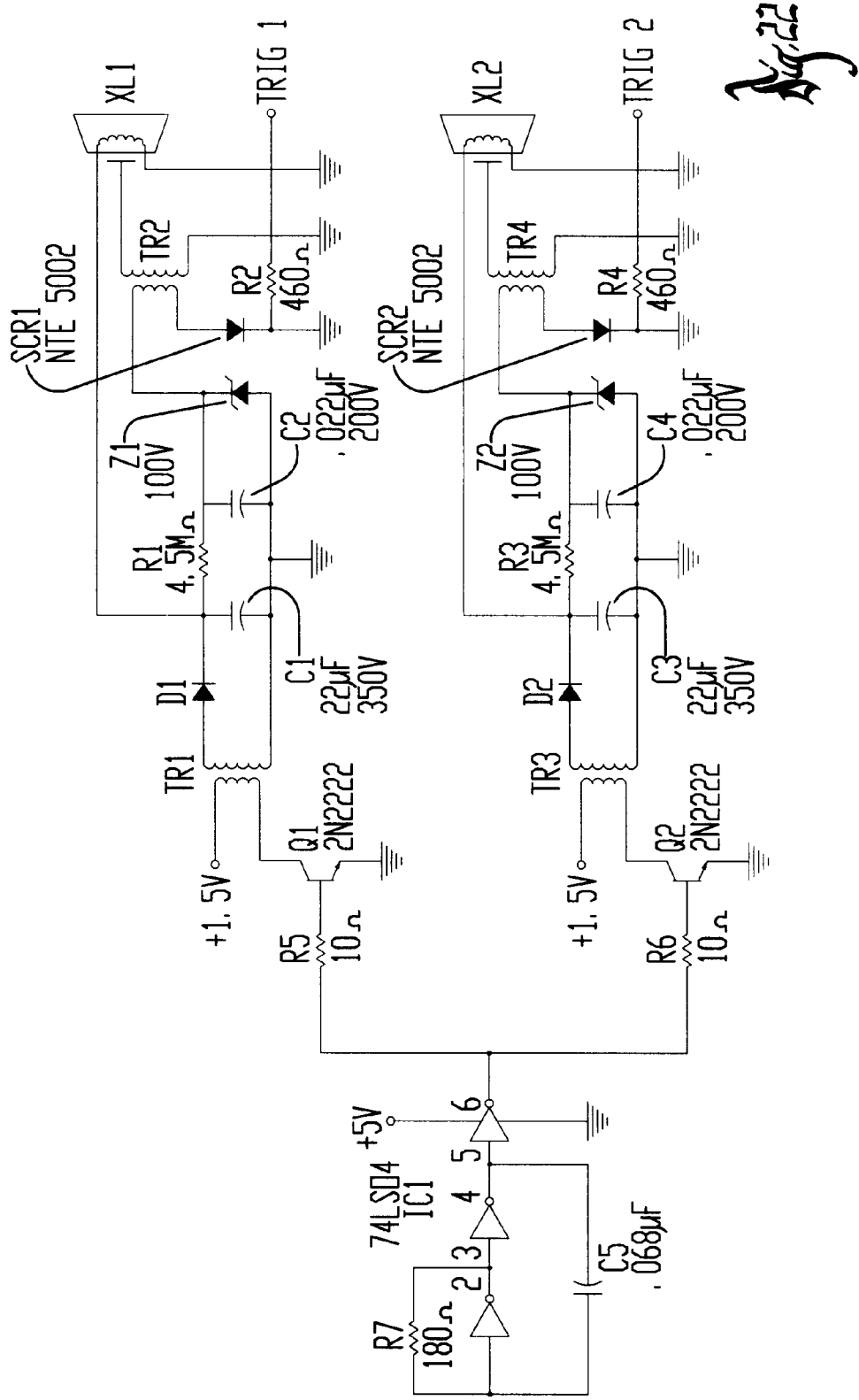
FIG. 22 is an electrical schematic of strobe light assembly circuit.

Referring now to a strobe circuit schematically shown in FIG. 22, a xenon flash board provides the circuitry necessary to precharge and then flash either of the two xenon flash tubes upon prescribed trigger inputs. Xenon is chosen as the preferred discharge gas in the flash tube because of its extremely high luminance (i.e., brightness) versus halogen or normal incandescent flash tubes.

The circuit illustrated by FIG. 22 functions as follows: IC1, R7 and C5 constitute an oscillator circuit which runs at a frequency of 60 hertz at 0 to +5 volts. The oscillator output (IC1, Pin6) drives transistor Q1 on then off in oscillatory fashion inducing a collector current which pulses voltages between +0.3 volts and +1.5 volts on the primary side of transformer TR1. Transformer TR1 has a high secondary to primary winding ratio and thus functions as a voltage amplifier. The secondary windings of TR1, together with dio D1, chop and amplify the voltage pulses induced from the primary of TR1 so that a voltage of +300 volts is developed across the positive terminal of electolidic capacitor C1. This +300 volts is also connected to the anode (positive) side of the xenon flash tube XL1 (which adjoins light emission port 124). The cathode (negative) side of the flash tube is connected to ground, thus an arc discharge voltage of 300 volts is presented across the terminals of the flash tube. Current limiting resister R1 reverse biases zener diode Z1 to its break down voltage of 100 volts so that in conjunction with capacitor C2, a regulated voltage of +100 volts is presented to the primary side of trigger transformer TR2 and thus the anode of the trigger switch SCR1. In order to trigger the flash circuit, a positive going (TTL level) pulse is presented to the gate of the trigger switch SCR1. This turns SCR1 on, thus creating a voltage spike of approximately +100 volts on the primary side of the trigger transformer TR2. TR2 has a high secondary to primary winding ratio so that it also acts as a voltage amplifier, thus creating a secondary voltage pulse of approximately +1,000 volts in response to the trigger pulse. This 1,000 volt pulse is applied to the trigger electrode of the xenon flash tube which, together with the +300 volt anode to cathode voltage, causes the xenon gas in the flash tube to ionize and then discharge completely as the voltage charge of electrolidic capacitor C1 is effectively shorted to ground through the flash tube. Xenon flash tube XL2 (which adjoins light emission port 126) works effectively the same way with its own set of corresponding circuitry.

It will be appreciated, however, that other circuits or means may be employed to operate the strobe lights so that the strobe lights are operably coupled to the digital camera 30 and operate to emit pulses of light from two separate locations in a synchronized fashion so that a first pulse of light illuminates an object when a first image is created and second pulse of light illuminates an object when a second image is created.

4.2.2.5 Creation of Glare-Free Digital Image Composite—The Algorithm

Digital images 212, 220 are archived by computer 50 for processing. While the following description is directed to glare removal by processing of only two images, it will be appreciated by those skilled in the art that digital image glare removal, according to the invention, may be practiced by processing more than two images.

Figure 21:
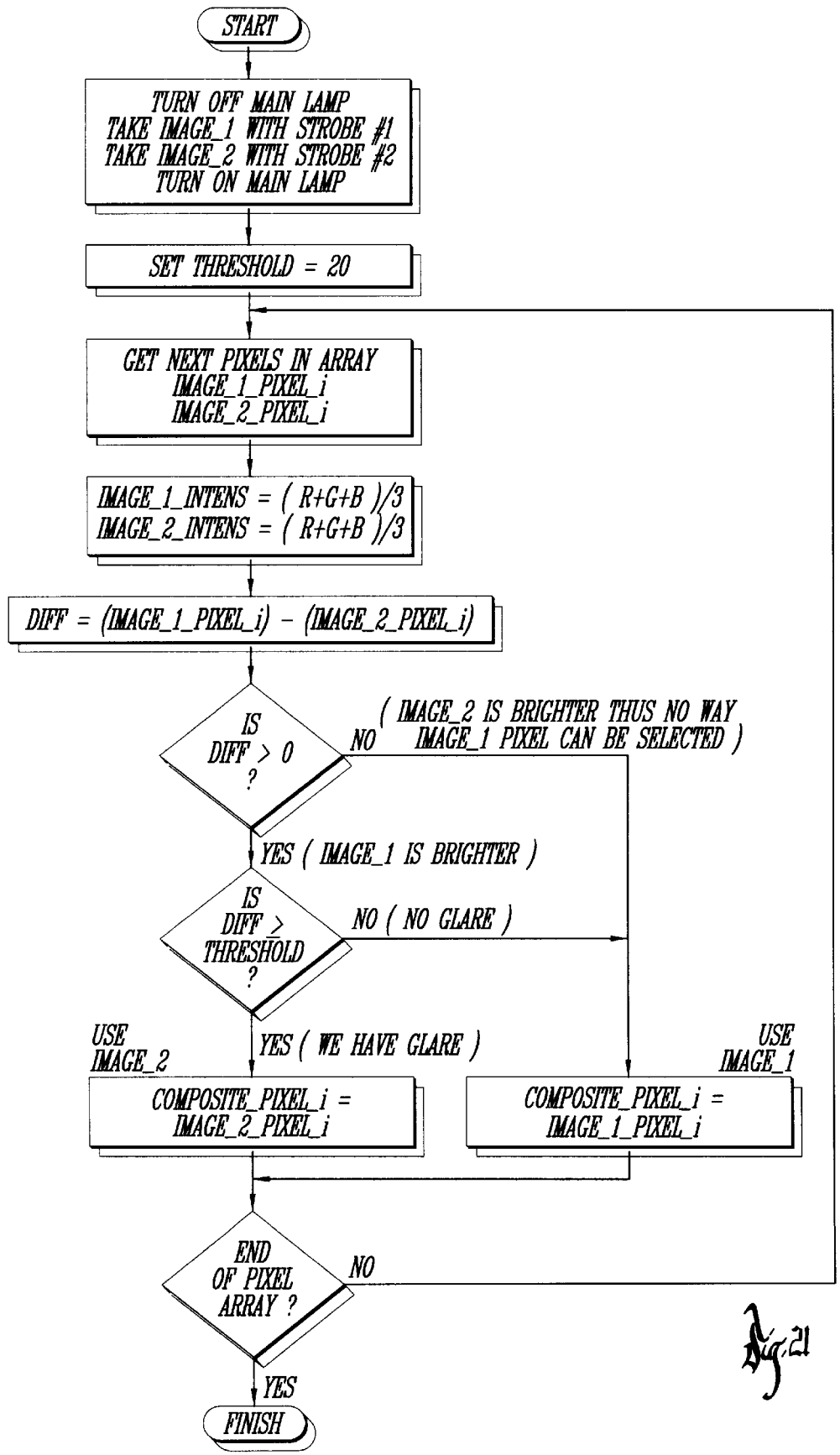
FIG. 21 is a flow chart depicting the software logic used to detect glare.

By way of example, there is illustrated in FIG. 21 a flow chart that describes the algorithm by which a glare-free composite image 230 can be generated by computer 50 through processing of images 212, 220.

When desired, an operator can initiate the following sequence which is manually initiated by trigger means (not shown) associated with frame grabber 40.

Upon initiation, frame grabber 40 signals via line 186 delay logic controller 142 to de-energize light 88 by means of an electrical circuit. Frame grabber 40 takes first image 212 which has been illuminated by strobe 120 from the video output of camera 30. Next, frame grabber 40 takes image 220 which has been illuminated by strobe 122 from camera 30 video output. Images 212 and 220 are immediately archived by computer 50.

An arbitrary glare threshold value is entered into the computer 50 which will be used to determine whether glare is present. A processing means, e.g., software or hardware, compares each pixel in the array associated with first image 212 to its corresponding pixel in second image 220. A difference is calculated by subtracting from the value associated with a pixel from first image 212 the value associated with the corresponding pixel in image 220. If the difference is greater than zero-indicating that the image 212 pixel is brighter than the corresponding pixel in image 220, the processing means will select the pixel from image 212 for use in the composite image 230. If the difference is less than zero-indicating that the pixel associated with image 212 is brighter-the processing means will compare the difference to the threshold value. If the difference is not greater than the threshold value-indicating that no glare is present, the processing means selects the pixel associated with first image 212 for use in the composite image 230.

If the difference is equal to or greater than the threshold value-indicating a glare condition, the processing means will select the pixel from second image 220 for use in creating composite image 230. The processing means will in this way cycle through a comparison of all pixels in both images to create composite 230. Composite 230 will then be archived by computer 50 for any desired use, including display on monitor 167, or printout on printer 168.

With the algorithm, the computer 50 is operable to identify pixels associated with first glare region 210 (FIG. 7) caused by glare 209 and second glare region 220 associated with glare 219.

Figure 11:
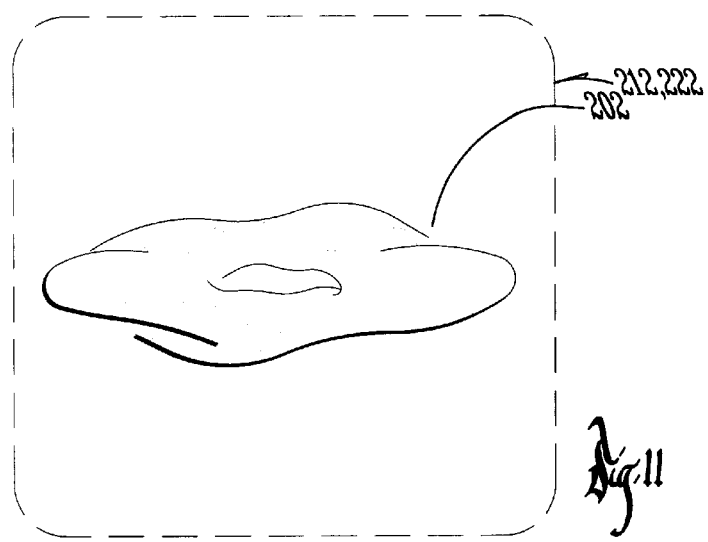

Referring to FIG. 10, a composite image is shown as being produced by removing glare region 220 from first digital image 212 and replacing it with non-glare region 221 from second digital image 220. Conversely, as shown in FIG. 11, a composite image may be created by removing glare region 222 from second digital image 220 and replacing it with non-glare region 223 from first digital image 212.

4.2.2.6 Example

Figure 12:
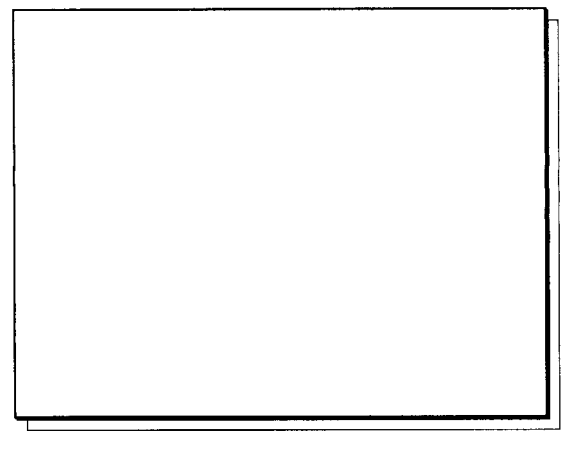
FIGS. 12–14 are a series of example images produced and displayed in accordance with an embodiment of the present invention.
Figure 13:
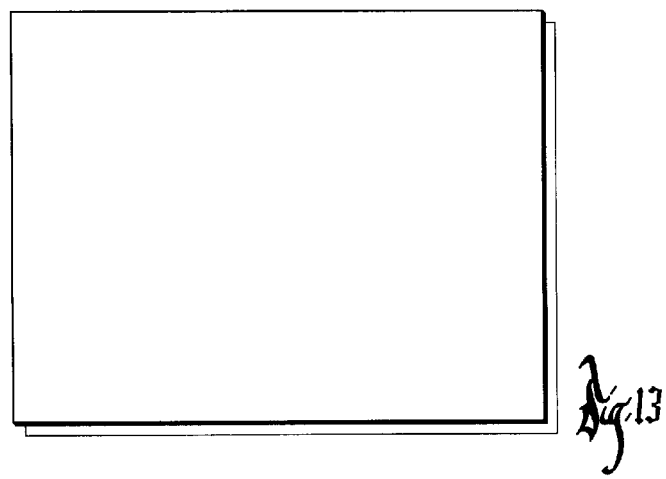
Figure 14:
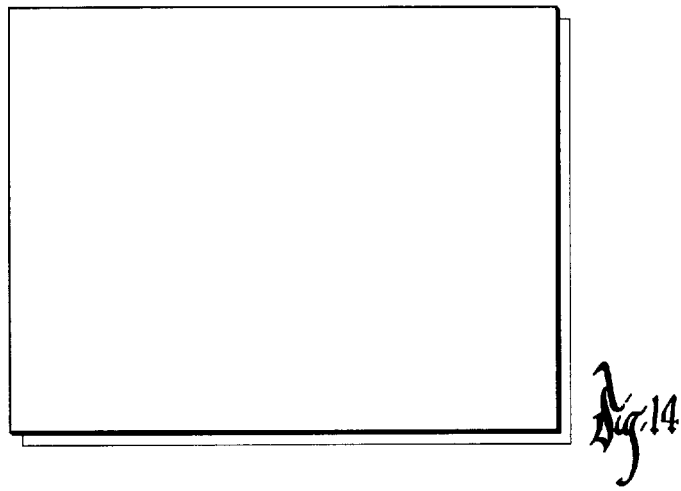

Referring to FIGS. 12–14, and Example is provided to demonstrate the efficacy of the invention.

Shown in FIGS. 12–14 are digital image reproductions of a cap used on a container of a popular orange juice product. The cap was chosen because its outer surface is glossy and, thus, resembles the light reflection properties of wet tissue.

Referring first to FIG. 14, a first glare region 300 is created in the digital image of the object when it is illuminated with a strobe light located at a first position. In FIG. 13, the object was illuminated with a strobe light located at a position different than that associated with the digital image in FIG. 14. Thus, glare region 302 is created in a region of the object different from that shown in FIG. 14.

FIG. 12 illustrates a composite digital image created from the images shown in FIGS. 13, 14, by means of the invention described above. It will be appreciated to those skilled in the art that the invention is effective in the elimination of veiling glare that might otherwise mask cancerous lesions, or other abnormalities, in a digital reproduction of cervical tissue.

4.3. Alternatives/Options

The included preferred embodiment is given by way of example only, and not by way of limitation to the invention, which is solely described by the claims herein. Variations obvious to one skilled in the art will be included within the invention defined by the claims.

4.3.1 Color Processing

In the application of the above glare removal algorithm to color digital images, the portion of the algorithm shown in FIG. 21 designated for "color" processing is simply inserted into the algorithm.

In the color processing algorithm, the control means compares each 24-bit color word of the first image to each corresponding 24-bit color word of the second image. To achieve this goal, the control means gets a 24-bit color word from the first image and corresponding 24-bit color word from the second image. Next, the control means averages the sum of the red-bite, the green-bite, and the blue-bite to calculate an intensity that will be associated with each 24-bit word. Then, the control means calculates the difference between the intensity associated with a 24-bit word from the first image and the corresponding 24-bit word from the second image. The difference is then used in the balance of the algorithm shown in FIG. 21.

4.3.2 Compositions from More Than Two Digital Images

As previously mentioned, composite images may be generated by processing more than two digital images as described above. For instance, a composite may be generated by combining non-glare regions of three separate digital images illuminated by strobe beams emanated from three separate locations.

4.3.3 Video Camera

The invention may also be practiced with a video camera that is mountable to the colposcope head 70 as a substitute for the digital camera 30, described above. The practice of the invention with a video camera in place of a digital camera would only require appropriate mounting fixtures for securing the video camera to the colposcope head 70 with appropriate electrical connections so that a video camera would serve the functions and objectives of the invention as described above.

4.3.4 Other Light Sources

With respect to illumination of an object, various light sources (frequencies and light intensities) may be employed to achieve a wide variety desired effects. For instance, FIG. 25 shows an alternative embodiment of the present invention wherein the optics fiber 392, 394 are operably attached to the control panel and at the other end to the lighting lens assemblies 392 which also operates as the strobe light assemblies.

4.3.5 Computer

Computer 50, and particularly user interface circuitry, is designed and configured to permit enhancement of digital images created with apparatus 10 for screening and diagnositic purposes. Conventional digital imaging enhancement techniques are employed to facilitate visualization of tissue texture, tissue and leision borderlines and tissue vascularity, all important components of cancer screening and diagnosis. Specific enhancement techniques include, but are not limited, to those disclosed. See, for example, Cristoforoni, M.D., Gerbaldo, M.D., Perino, M.D., Piccoli, M.D., and Capitanio, M.D., *Computerized Colposcopy: Results of a Piolot Study and Analysis of Its Clinical Relevance,* Obstetrics & Gynecology, Vol. 85, No. 6, (June 1995); Contini, M.D., Zobbi, M.D., Pasquinucci, M.D., *Colposcopy and Computer Graphic: A New Method?*, AM J Obstet Gynecol (1989); Shafi, Dunn, Chenoy, Buxton, Williams, Luesley, *Digital Imaging Colposcopy. Image Analysis and Quantification of the Colposcopic Image,* British Journal of Obestrics and Gynecology, Vol. 101, pp. 234–238, (March 1994); Mikhail, M.D., Merkatz, M.D., and Romney, M.D., *Clinical Usefulness of Computerized Colposcopy: Image Analysis and Conservative Management of Mild Dysplasia,* Obstetrics & Gynecology, Vol. 80, No. 1 (July 1992), all teaching of which are hereby incorporated by reference.

4.3.6 Other Applications for Glare Removal

It will be appreciated that the glare-removal functionality of the invention described above may be employed as a cancer-detection technique directed to virtually any type of tissue which, when photographed in situ, suffers the veiling glare problems described above. In fact, the glare removal technique and apparatus described above may generally be employed for the topological mapping of the acetowhitening affects on cervical tissue, topological mapping of cervical vascularity and other potentially cancerous tissue vascularity, topological mapping of glycogen content of cervical tissue, and measurement of cervical anatomy.

What is claimed is:

1. An apparatus for glare removal in digital imaging of a cervix, comprising:
   a. digital camera operable to create at least first and second digital images of a portion of the cervix, the digital images having substantially the same field of view;

b. lights associated with the camera for illuminating the cervix with light pulses emitted from at least two locations, said lights operable to synchronize the emission of the pulses so that the cervix is illuminated with a first pulse for the creation of the first image and the cervix is illuminated with a second pulse for the creation of the second image, first glare and first non-glare regions created by the first pulse in the first image, each of said first glare and first non-glare regions comprising at least one digital element, second glare and second non-glare regions created by the second pulse in the second image; each of said second glare and second non-glare regions comprising at least one digital element, and c. digital processing means operable to create a glare-free digital composite image by replacing the at least one digital element of the glare region of the first image with the corresponding at least one digital element from the non-glare region of the second image.

2. The apparatus according to claim 1, wherein each image comprises an array of discreet digital image elements, each image element of the first image having a spatially identical corresponding element in at least the second image, and wherein the lights comprise a pair of lights separated by a distance, the distance separating the pair of lights being sufficient so that the first glare region associated with the first image comprises a set of image elements different than the second glare region associated with the second image.

3. The apparatus according to claim 1, wherein the lights comprise strobe lights.

4. The apparatus according to claim 1, wherein said camera is operably coupled to a colposcope having a beam splitter.

5. The apparatus according to claim 1, wherein the digital processing means comprises a computer software and hardware system.

6. The apparatus according to claim 1, wherein said camera is configured to create monochrome digital images.

7. The apparatus according to claim 1, wherein the digital camera is configured to create color digital images.

8. The apparatus according to claim 1, wherein the digital camera is configured with a single CCD digital imaging chip.

9. The apparatus according to claim 1, wherein the digital camera is configured with at least three CCD digital imaging chips to generate color digital images.

10. The apparatus according to claim 1, wherein said digital processing means is operable to create a glare-free digital composite image by means of comparing on a pixel-by-pixel basis the digital image elements comprising each digital image.

11. A method for glare removal in digital imaging of the cervix useful in cervical cancer detection, comprising:

a. creating at least first and second digital images of a portion of the cervix, each digital image having substantially the same field of view;

b. illuminating the cervix with light pulses emitted from at least two different locations, the illumination occurring by means of lights operable to synchronize the emission of the light pulses so that the cervix is illuminated with the first pulse for the creation of the first image and the cervix is illuminated with the second pulse for the creation of the second image to create first and second glare and non-glare regions in the first and second images, respectively, created by the first and second pulses, respectively; each of said first and second glare and non-glare regions comprising at least one digital element, and c. creating a glare-free digital composite image by replacing the at least one digital element associated with the glare region of one image with the corresponding at least one digital element from the non-glare region of the other image.

12. A method for glare removal in digital imaging of a cervix useful in cervical cancer detection comprising:

a. creating at least a first and second digital image of the cervix;

each said image comprising an array of discreet digital image elements, each element of each image having a spatially identical corresponding element in the other image, the first image further comprising a first object image region in the array of image elements, the second image further comprising a second object image region in the array of image elements, the image elements comprising the first object image region being substantially the same as the digital image elements comprising the second object image region;

b. illuminating the cervix with at least a first and second light pulse emitted from a first and second strobe light, respectively, said first and second strobe lights located at first and second remote locations, said strobe lights operable to initiate and terminate said beams, said strobe lights operable to synchronize the initiation and termination of each beam so that the object is illuminated with said first pulse for the capture of the first image and the object is illuminated with the second pulse for the capture of the second image, first glare and non-glare regions created by said first beam in the array of digital elements of the first image, second glare and non-glare regions created by said second beam in the array of digital elements in the second image;

d. a distance between the first and second strobe locations sufficient so that the first glare region comprises a region of image elements different from that comprising the second glare region; and e. creating a glare-free digital composite image through digital processing by replacing the digital elements of the glare region of one image with the corresponding elements of the non-glare region of the other image.

13. An apparatus for glare removal in digital imaging of in situ tissue, comprising:

a. digital imaging means operable to create at least a first and second digital image of the object, each said image comprising an array of discrete digital image elements, each element of each image having a spatially identical corresponding element in the other image, a first tissue image region created by said imaging means in the array of image elements in the first image, a second tissue image region created by said imaging means in the array of image elements in the second image, the image elements comprising the first tissue image region being substantially the same as the digital image elements comprising the second tissue image region;

b. strobe light means for illuminating the tissue with at least a first and second light pulse emitted from a first and second strobe location, respectively; said first and second locations being separated by a distance, said strobe light means operable to initiate and terminate said beams, said strobe light means operable to synchronize the initiation and termination of each beam so that the tissue is illuminated with said first pulse for the capture of the first image and the tissue is illuminated with the second pulse for the capture of the second image, first glare and non-glare regions created by said first beam in the array of digital elements of the first image, second glare and non-glare regions created by said second beam in the array of digital elements of the second image;

c. said distance between the first and second strobe locations sufficient so that the first glare region comprises a region of image elements different from that comprising the second glare region; and d. digital processing means operable to create a glare-free digital composite image by replacing the digital elements of the glare region of one image with the corresponding elements from non-glare regions of the other image.

* * * * *